(12) United States Patent
Norris (10) Patent No.: US 8,162,852 B2
(45) Date of Patent: Apr. 24, 2012

(54) METHODS FOR MEDICAL DEVICE ALIGNMENT

(75) Inventor: Perry R. Norris, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 275 days.

(21) Appl. No.: 12/256,485

(22) Filed: Oct. 23, 2008

(65) Prior Publication Data

US 2010/0106056 A1 Apr. 29, 2010

(51) Int. Cl.
*A61B 10/00* (2006.01)

(52) U.S. Cl. ........................................ 600/567; 600/586

(58) Field of Classification Search .................. 600/562, 600/567, 108, 112, 114, 160, 178–182; 606/2, 606/46
See application file for complete search history.

(56) References Cited

U.S. PATENT DOCUMENTS

| | | | |
|---|---|---|---|
| 4,321,551 A | 3/1982 | Bleil et al. | |
| 5,320,110 A * | 6/1994 | Wang | 600/566 |
| 5,526,822 A | 6/1996 | Burbank et al. | |
| 5,598,269 A * | 1/1997 | Kitaevich et al. | 356/399 |
| 5,751,869 A * | 5/1998 | Li et al. | 385/33 |
| 5,810,541 A | 9/1998 | Casey et al. | |
| 5,810,841 A * | 9/1998 | McNeirney et al. | 606/130 |
| 5,855,554 A | 1/1999 | Schneider et al. | |
| 5,976,092 A * | 11/1999 | Chinn | 600/459 |
| 6,007,497 A | 12/1999 | Huitema | |
| 6,069,748 A | 5/2000 | Bietry | |
| 6,086,544 A | 7/2000 | Hibner et al. | |
| 6,203,498 B1 | 3/2001 | Bunce et al. | |
| 6,273,862 B1 | 8/2001 | Privitera et al. | |
| 6,364,839 B1 | 4/2002 | Little et al. | |
| D461,895 S | 8/2002 | Barnes et al. | |
| 6,428,487 B1 | 8/2002 | Burdorff et al. | |
| 6,471,651 B1 | 10/2002 | Hwang et al. | |
| 6,605,095 B2 * | 8/2003 | Grossman | 606/130 |
| 6,688,758 B2 | 2/2004 | Thibault | |
| 6,689,067 B2 * | 2/2004 | Sauer et al. | 600/464 |
| 6,692,200 B2 | 2/2004 | Peterson | |
| 6,702,749 B2 | 3/2004 | Paladini et al. | |
| 6,752,768 B2 | 6/2004 | Burdorff et al. | |

(Continued)

FOREIGN PATENT DOCUMENTS

EP 1932481 6/2008

(Continued)

OTHER PUBLICATIONS

"Application Engineering Note-Multimode Fiber Compatibility, Application Note," Corning, Supersedes (Apr. 2005) pp. 1-5.

(Continued)

*Primary Examiner* — Nicholas Lucchesi
*Assistant Examiner* — Melissa A Snyder
(74) *Attorney, Agent, or Firm* — Frost Brown Todd LLC (57) ABSTRACT

A device and method for aligning medical devices is disclosed. A biopsy device having a handpiece, an elongated hollow needle with a lateral tissue receiving port, and an apparatus for providing a guide path, such as a light apparatus, is described. The light apparatus can provide visible light in a generally planar form, and the hollow needle can be aligned with the plane of light provided by the light apparatus. The light guide path provides a visible path along the skin of a patient, and the path can be used to align the needle of the biopsy device with a separate, hand held probe, such as an ultrasound probe used in ultrasound imaging.

10 Claims, 5 Drawing Sheets

U.S. PATENT DOCUMENTS

| | | | |
|---|---|---|---|
| 7,024,791 | B2 | 4/2006 | Marshall et al. |
| 7,031,367 | B2 | 4/2006 | Marshall et al. |
| 7,041,058 | B2 | 5/2006 | Piehler |
| 7,269,907 | B2 | 9/2007 | Levine et al. |
| 7,303,530 | B2 | 12/2007 | Barnes et al. |
| 7,310,887 | B2 | 12/2007 | Nash et al. |
| 7,367,945 | B2 | 5/2008 | Dasgupta et al. |
| 7,416,533 | B2 | 8/2008 | Gellman et al. |
| 7,858,038 | B2 | 12/2010 | Andreyko et al. |
| 2003/0069502 | A1 | 4/2003 | Makin et al. |
| 2003/0199753 | A1 | 10/2003 | Hibner et al. |
| 2003/0199754 | A1 | 10/2003 | Hibner et al. |
| 2003/0199785 | A1 | 10/2003 | Hibner et al. |
| 2004/0034280 | A1 | 2/2004 | Privitera et al. |
| 2004/0077972 | A1 | 4/2004 | Tsonton et al. |
| 2004/0106934 | A1 | 6/2004 | Grossman |
| 2004/0249278 | A1 | 12/2004 | Krause |
| 2005/0065453 | A1 | 3/2005 | Shabaz et al. |
| 2005/0131291 | A1 | 6/2005 | Floyd et al. |
| 2006/0144548 | A1 | 7/2006 | Beckman et al. |
| 2006/0200041 | A1 | 9/2006 | Weikel et al. |
| 2007/0049822 | A1 | 3/2007 | Bunce et al. |
| 2007/0149878 | A1 | 6/2007 | Hankins |
| 2007/0167736 | A1 | 7/2007 | Dietz et al. |
| 2007/0232953 | A1 | 10/2007 | Dietz et al. |
| 2008/0015429 | A1 | 1/2008 | Tsonton et al. |
| 2008/0146915 | A1* | 6/2008 | McMorrow .................. 600/424 |
| 2011/0125055 | A1 | 5/2011 | Privitera et al. |

FOREIGN PATENT DOCUMENTS

WO    WO 2008/120137    10/2008

OTHER PUBLICATIONS

"Line Generator Diode Lasers Modules," Coherent, http://www.coherent.com/products/?984/Line-Generator-Diode-Laser-Modules, printed Nov. 11, 2011.

"Structured Light Lasers," StockerYale, www.stockeryale.com/lasers, pp. 1-2, printed Nov. 11, 2011.

* cited by examiner

METHODS FOR MEDICAL DEVICE ALIGNMENT

CROSS REFERENCE TO RELATED APPLICATION

This Application cross-references and incorporates by reference U.S. Patent Application "Medical Device Alignment" filed in the name of Perry Norris and having a common filing date.

BACKGROUND

Biopsy samples have been obtained in a variety of ways in various medical procedures using a variety of devices. One such biopsy device useful in obtaining breast biopsy tissue samples is the MAMMOTOME® brand biopsy device from Ethicon Endo-Surgery, Inc. of Cincinnati, Ohio. Biopsy devices may be used win connection with or under various imaging systems, such as stereotactic (X-Ray) guidance, ultrasound guidance, and/or MRI guidance. Various biopsy devices are disclosed in U.S. Pat. No. 5,526,822, issued Jun. 18, 1996; U.S. Pat. No. 6,086,544, issued Jul. 11, 2000; U.S. Pat. No. 6,752,768, issued Jun. 22, 2004; and "U.S. Non-Provisional patent application Ser. No. 11/942,785, entitled "Revolving Tissue Sample Holder for Biopsy Device," filed Nov. 21, 2007. U.S. Pat. No. 6,273,862 issued Aug. 14, 2001 and U.S. Pat. No. 6,428,487 issued Aug. 6, 2002 disclose one or more handheld biopsy devices which can be used with various imaging systems, including ultrasound guidance. The entire disclosure of each of the above-cited U.S. Patent documents is incorporated by reference herein.

Ultrasound diagnostic instruments are known for use in diagnostic procedures, including in imaging for obtaining biopsy samples. The following U.S. Patent documents disclose methods and/or devices useful in ultrasound procedures: U.S. D461,895 issued Aug. 20, 2002; US 2007/0049822 published Mar. 1, 2007; U.S. Pat. No. 6,203,498 issued Mar. 20, 2001; U.S. Pat. No. 6,364,839 issued Apr. 2, 2002; U.S. Pat. No. 6,471,651 issued Oct. 29, 2002; U.S. Pat. No. 7,041,058 issued May 9, 2006; U.S. Pat. No. 7,303,530 issued Dec. 4, 2007; U.S. Pat. No. 7,367,945 issued May 6, 2008. The entire disclosure of each of the above-cited U.S. Patent documents is incorporated by reference herein.

When taking a biopsy sample using a biopsy device having outer needle with a tissue receiving port and in internal cutter, it can be desirable to image the needle as well as the tissue to be sampled. For instance, when using ultrasound imaging, it can be desirable to insert the needle and view the position of the needle with respect to a lesion under ultrasound guidance.

SUMMARY OF THE INVENTION

Applicant has recognized the desirability of providing a device and method for aligning a biopsy device, such as a handheld biopsy device, with respect to a component of an imaging device, such as a handheld probe of an ultrasound imaging system. Applicant has also recognized the desirability of providing such alignment without mechanically or otherwise physically connecting a handheld biopsy device with a handheld probe.

In one embodiment, the invention provides a biopsy device having a component that provides a guide path, such as a light source for providing a guide path extending distally from a biopsy needle.

In another embodiment, the invention provides a method for aligning at least one medical device. The method can include projecting a guide path, such as a light guide path, from a first handheld medical device, such as a biopsy device, and aligning a portion of the biopsy device with a second handheld medical device, such as a handheld imaging probe.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive. For example, the following description is provided with respect to use with handheld biopsy devices useful in ultrasound imaging environments, but the invention can also be employed with other medical devices, including other biopsy devices used in X-ray, MRI, PET, PEM, BSGI (breast specific gamma ray imaging) and other imaging modalities. Additionally, while the disclosure below is directed generally to providing laser light guide paths, it will be understood that other light sources capable of providing a guide path or defined pattern, such as by focusing or otherwise directing light to illuminate a defined linear or curvilinear path or pattern along the skin, tissue, or organ of a patient could be employed.

Referring to FIGS. 1-4, a biopsy device 10 is shown being used to obtain a breast biopsy sample from a patient's breast 2. The biopsy device 10 is shown having a lightweight, ergonomically shaped handpiece 20 that can be grasped and manipulated by a single hand of a user. An elongated biopsy needle 30 extends proximally from a distal end of the handpiece. The handpiece and biopsy needle can be fully disposable, or alternatively, a portion of the handpiece can be reusable, and the needle and a portion of the handpiece, including the portion from which the needle extends, can be disposable.

Figure 4:
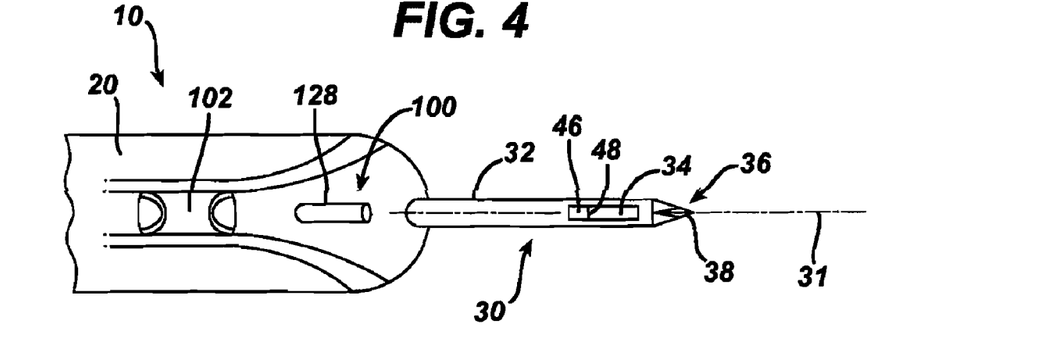
FIG. 4 illustrates a top view of the distal portion of the biopsy device of the type shown in FIG. 1, illustrating how a light source such as a laser light source can be disposed on the handpiece of the biopsy device to provide a guide path that is generally parallel to the longitudinal axis of the biopsy needle, and which generally bisects a lateral tissue receiving opening in the biopsy device.

The biopsy needle 30 can comprise an outer cannula 32 having side tissue receiving opening 34 and a closed distal end having a tissue piercing tip 36. The tissue receiving opening 34 can face upwardly, or vertically (toward the reader as viewed in FIG. 4). The tip 36 can include a generally flat blade 38, which can be aligned generally vertically. The biopsy device can include a cannular cutter 46 (FIG. 4) having a cutting edge 48. The cutter 46 can be adapted to translate and rotate within the outer cannula 32. Tissue received in the opening 34 (such as by being drawn into opening 34 by vacuum) can be severed by the cutting edge 48 as the cutter is translated across the length of opening 34. In FIG. 4, the distal portion of the cutter 46 is seen through the opening 34. One biopsy device having such an outer cannula and inner cutter is a Mammotome® brand biopsy device marketed by Ethicon Endo-Surgery, Inc. The Biopsy device can also include a tissue storage assembly 50 disposed at a distal end of the biopsy device, for holding tissue samples obtained by severing tissue received in opening 34.

According to one embodiment of the present invention, the handpiece 20 includes a component for providing a guide path. The component can comprise a light source 100 adapted to project an illuminated guide path on skin of a patient undergoing a biopsy (or on a drape or sheet covering the patient). The light source 100 can be mounted or otherwise disposed on a distal portion of the handpiece 20, such as on a reusable portion of the handpiece, and can direct light in a distal direction in a plane or fan shaped sheet that is generally parallel to and aligned with the long axis of the needle 30 (the axis indicated by reference number 31 in FIG. 4).

The light source 100 can be activated by any suitable switch or control, such as a by a finger activated control switch 102 disposed on an upper surface of the handpiece 20. The light source 100 can be powered by any suitable power supply, including by batteries carried in the handpiece 20, or by a power cord extending from the handpiece.

The light source 100 can comprise a laser line generator adapted to provide a generally planar, fan-shaped sheet of light (indicated by numeral 120 in FIG. 1) in a distal direction along at least a portion of the needle 30, such that the intersection of the light provided by source 100 with a surface (such as an outer surface of the needle 30 or the outer surface of the patient's skin) provides a guide path indicated by numeral 124. As viewed in FIG. 4, the sheet of light 120 provided by light source 100 extends along and is aligned with axis 31, and when light source 100 is activated, the sheet of light 120 can substantially bisect the opening 34.

The term "guide path" as used herein means a visible path having a width and length, with the length being at least 10 times the maximum width, and such that a direction or orientation is readily discernable from viewing the path. In one embodiment, the length of the guide path provided is at least 50 times the maximum width of the guide path.

The guide path can be in the form of either a continuous line (straight, curved, or combination of straight and curved lines), or a series of closely spaced together discrete segments (such as a series of closely spaced dots, circles, dashes, crosses or other suitable shapes) which when viewed together from the distance mentioned below (2 feet) indicate a path direction to the viewer.

As used herein, "visible" as used in connection with a path means that a path can be seen by an observer with unmagnified and otherwise unamplified or augmentetd normal color vision (20/20) when the path is projected on a planar flat non-glossy white surface (if the path is not white, otherwise if the path is white, on planar flat black surface) in a darkened room and viewed at a distance of 2 feet from the observer. It will be understood that the previous sentence is for purpose of helping the reader understand what the term "visible" means in the context of the present invention, and that a device according to the present invention can be used to provide a guide path that can be seen under other lighting conditions, including ambient lighting, or the reduced lighting typical of an operating room, as well as in a dark room.

The guide path can have a specific color, such as a reddish hue, a greenish hue, a bluish hue, or any other suitable color or combination of colors, such as white. In one embodiment, the guide path 124 can have a maximum width of no more than about 5 mm, and in one embodiment can be less than about 2 mm wide, such as a guide path having a maximum width between about 0.5 mm and about 1.5 millimeter. In another non-limiting alternative embodiment, the guide path can have a width of between about 5 mm and about 10 mm.

The maximum width of the guide path can be less than the maximum diameter of the needle 30, and in one embodiment is less than half the diameter of the needle. In one embodiment, the guide path is visible as a generally continuous straight or curved line having a generally uniform line width of less than about 2 mm.

Figure 4A:
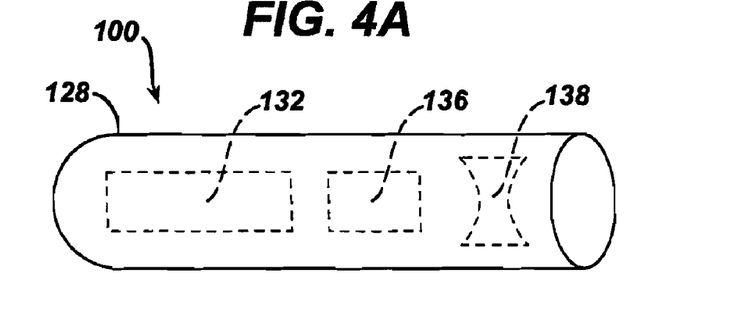
FIG. 4A illustrates a laser light source including a laser diode, a collimator, and a lens disposed within a housing.

The light source 100 can comprise a laser light source, such as laser line generator. Referring to FIG. 4A, the light source 100 can include a housing 128, a laser diode 132 disposed in the housing for generating a laser beam, a collimating lens 136, and a lens 138, such as a cylindrical lens, for diverging the collimated beam to provide a generally planar sheet or fan of laser light, which provides a guide path when the sheet of light intersects a surface (such as the patient's skin). It will be understood that other methods for providing a generally planar sheet or fan of laser light can also be employed, including using moving or "scanning" laser beams, rotating mirrors, and multiple laser source.

The light source 100 can be permanently joined to the handpiece 20, such as by being fastened or built into an outside covering of the handpiece 20, or alternatively, the light source can be removably supported on the handpiece so that the light source can be detached if desired. The light source 100 can be supported on the handpiece to have one orientation, or alternatively, the light source 100 can be pivotably supported (or supported on a ball and socket type support) so that the direction of the light projected from light source 100 can be varied.

Laser line generators are commercially available having various diode power levels, wavelengths, and fan angles. For instance, but without limitation, the light source 100 can comprise a laser line generator having a fan angle of between about 15 degrees and about 90 degrees, a diode power level less than about 150 milliwatts, and a wavelength of between about 350 to about 850 nanometers. Laser line generators are available from various commercial sources, such as for instance: StockerYale of Salem New Hamphire (www.stockeryale.com), including Mini Laser products having a diode power of between 1-40 milliWatts and a wavelength of between about 635-830 nanometers, Telecentric Micro-Focus Laser products having a diode power of about 100 mW and a wavelength of about 660 nm, and Green Laser products having a diode power of about 1 to about 20 mW and a wavelength of about 532 nm; and Coherent, Inc. products designated as LG2 635 nm 2 mW 60 and LG3 635 nm 1.5 mW 40 (www.Coherent.com).

The following patent documents are incorporated by reference in their entirety for their disclosure related to lasers and laser line generators: U.S. Pat. No. 6,069,748 issued May 30, 2000; U.S. Pat. No. 6,688,758 issued Feb. 10, 2004; U.S. Pat. No. 7,024,791 issued Apr. 11, 2006; U.S. Pat. No. 7,310,887 issued Dec. 25, 2007; U.S. Pat. No. 7,269,907 issued Sep. 18, 2007; U.S. Pat. No. 7,031,367 issued Apr. 18, 2006.

Alternatively, other light sources may be used with suitable focusing, directing, collimating, and/or concentrating shaping devices (e.g. lens, collimator, mirror, and other components) to focus, direct, collimate, concentrate and/or otherwise shape light to provide a visible guide path.

Figures 1, 2:
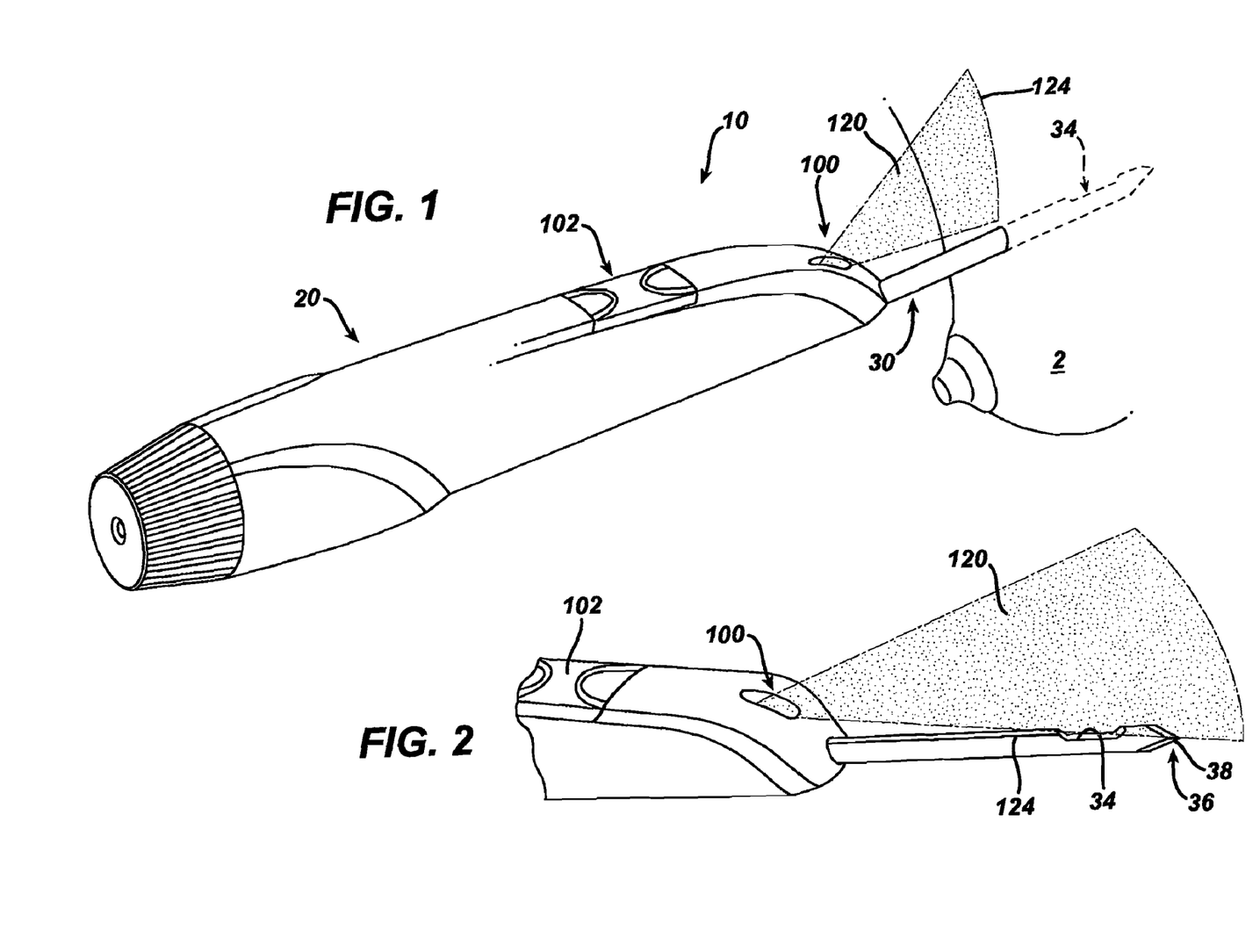
FIG. 1 illustrates a biopsy device having a laser line generator for providing a guide path on the outer surface of a patient's breast.
FIG. 2 illustrates a distal portion of the biopsy device shown in FIG. 1.
Figure 3:
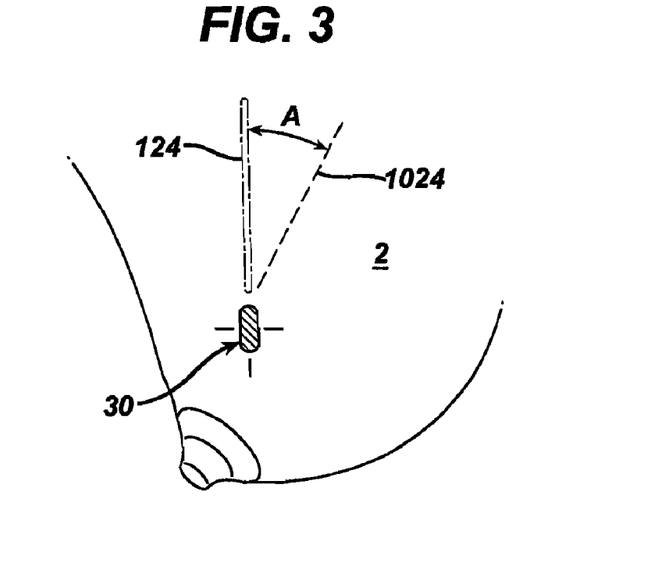
FIG. 3 illustrates a guide path for providing proper alignment of a hand held transducer, such as an ultrasound probe, with respect to a biopsy needle of a biopsy device of the type shown in FIG. 1, and also depicts the guide path aligned to be generally parallel to and aligned with major axis of a non-circular cross-section of a biopsy needle.

As schematically illustrated in FIG. 3, the cross-section of the biopsy needle can be non-circular, and can have a major axis aligned generally vertically and a minor axis aligned generally horizontally. The light source 100 can provide a generally planar sheet of light 120 which extends in a vertical plane generally parallel to and aligned with the major axis of the cross section of needle 30. Accordingly, the guide path 124, as visible on the patient's skin, can also indicate the orientation of the tissue receiving opening 34 when the tissue receiving opening 34 is disposed beneath the outer layer of the patient's skin (as in FIG. 1).

Still referring to FIG. 3, the guide path 124 provided by the intersection of the sheet of light 120 and the patient's outer skin can be used to orient the needle 30 with respect to a separate handheld medical device, such as an ultrasound probe. In FIG. 3, the correct line of alignment of an ultrasound transducer with respect to the needle 30 is indicated by the guide path 124, while an incorrect line of alignment is indicated by dotted line 1024, with the angle between the two orientations indicated by angle A.

Figure 5:
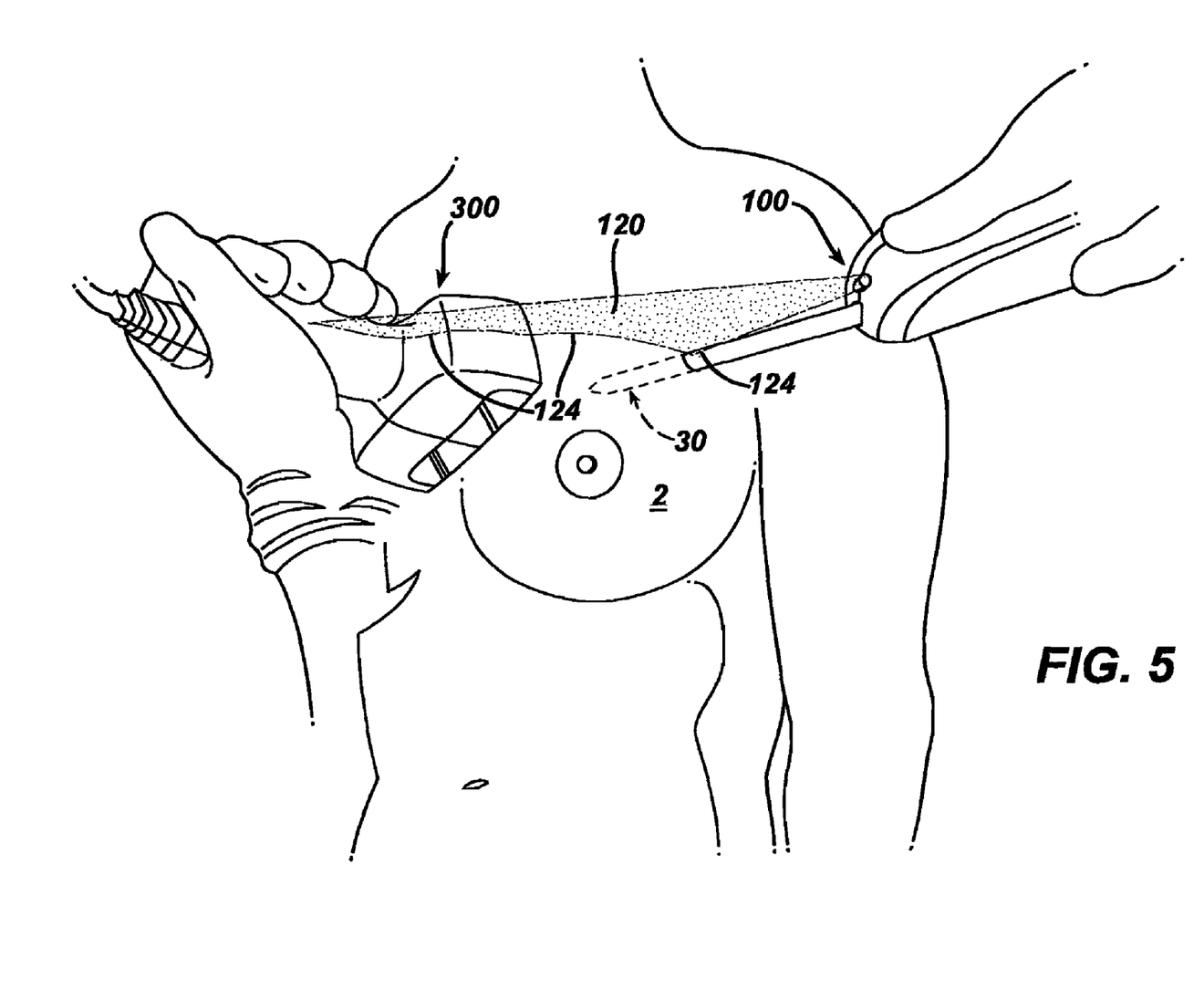
FIG. 5 illustrates a biopsy device having a laser line generator for providing a guide path extending from the biopsy device along an outer surface of a patient's breast, and how the biopsy device can be held in one hand while a hand held transducer, such as an ultrasound probe, can be held in the other hand, with the guide path providing for correct alignment of the long axis of the transducer with respect to the biopsy device needle.

When attempting to image the biopsy needle opening 34 and adjacent biopsy site within the patient's breast with ultrasound, it can be desirable to align the axis 31 of the needle 30 as closely as possible with the axis of the ultrasound probe transducer. Referring to FIG. 5, a perspective view is provided to illustrate how the light plane 120 provided by laser light source 100 intersects the needle 30, the breast 2, and a separate handheld ultrasound probe 300, to provide a light guide path 124 which has a segment visible along a portion of the needle positioned outside the breast, a segment of the path 124 visible along the patient's breast between the insertion point of the needle and the probe 300, and a segment of the path 124 visible along a portion of a handheld ultrasound probe 300.

Prior to inserting the needle 30 into the patient's tissue, the probe 300 and the needle 30 can be aligned with guide path 120. The needle can then be inserted into the patient's tissue under ultrasonic imaging. Alternatively, after inserting the needle into the patient, the guide path 120 can be used to align the probe 300 to image the needle and adjacent tissue.

Figure 6:
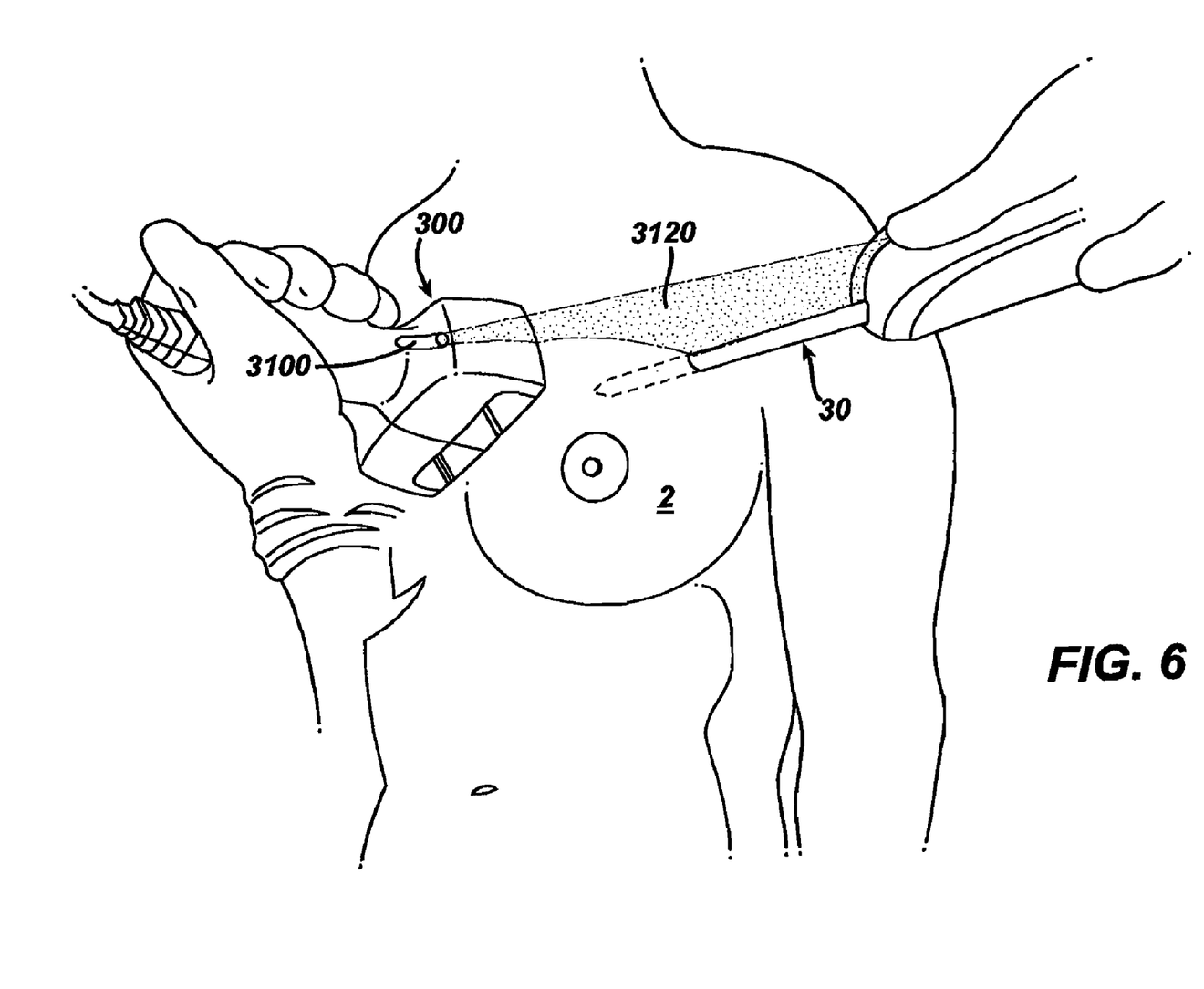
FIG. 6 depicts an alternative arrangement where the handheld probe comprises a laser line generator.

FIG. 6 illustrates an alternative embodiment, where the ultrasound probe 300 includes a light source 3100, and the light source 3100 provides a generally planar sheet of light 3120 extending from the probe 300 toward the needle 30. In still another variation, a separate device can be used to provide a guide path for aligning the probe 300 and the needle 30.

If desired, multiple laser light sources can be disposed on the biopsy device 10, the probe 300, a separate device (e.g. a separate hand held device or a separate fixed or mounted device), or multiple laser light sources can be disposed on both the device 10 and the probe 300. For instance, a second laser light source can be disposed on the probe 300 shown in FIG. 6 to provide a light guide path at right angles to the light path provided by light source 3100.

Figure 7:
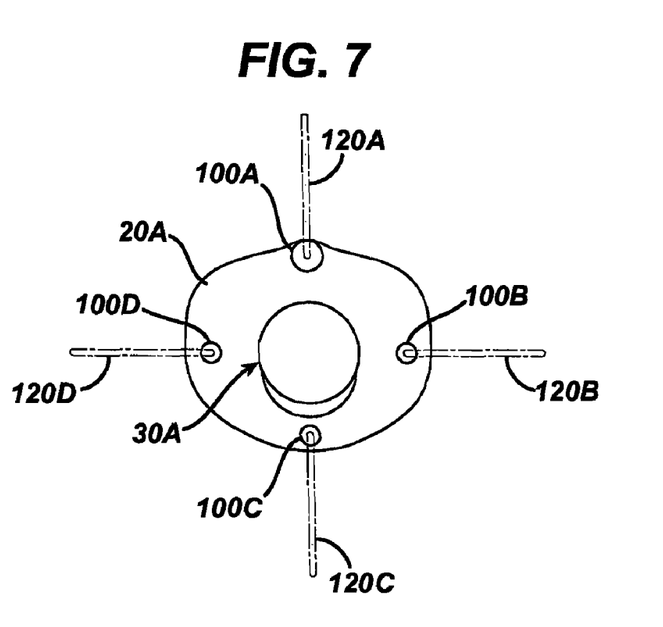
FIG. 7 is a front view of an alternative embodiment of a biopsy device according to the present invention.

FIG. 7 illustrates a front view of an alternative handpiece 20A, the handpiece 20A including laser light sources 100A-100D. The light sources are positioned at multiple locations around the circumference of the handpiece to provide a fan of light 120A associated with the top of the needle 30 (ie.at 12 o'clock), a fan of light 120B and fan of light 120D associated with the sides of the needle (i.e at 3 and 9 o'clock), and a fan of light 120C associated with the bottom of the needle (i.e. at 6 o'clock'). The four laser light sources 100A-100D can each provide a different color of laser light to provide light paths, each having a different hue. Alternatively, a beam splitter or other suitable device can be employed to split laser light from one source to provide multiple guide paths.

In a stereotactic application, such as for use in x-ray mammography, a biopsy device can include a generally stationary housing comprising a mount for supporting the housing with respect to a table or x-ray source, a rotatable needle, and a firing mechanism for firing the needle into tissue, as is shown in U.S. Pat. No. 6,007,497 issued Dec. 28, 1999, and incorporated herein by reference. In accordance with one application of the present invention, one or more laser light sources can be disposed on the housing, or other fixed component, to provide one or more light guide paths on the patient's breast, which guide paths can be fixed with respect to the needle's rotation.

Figure 8:
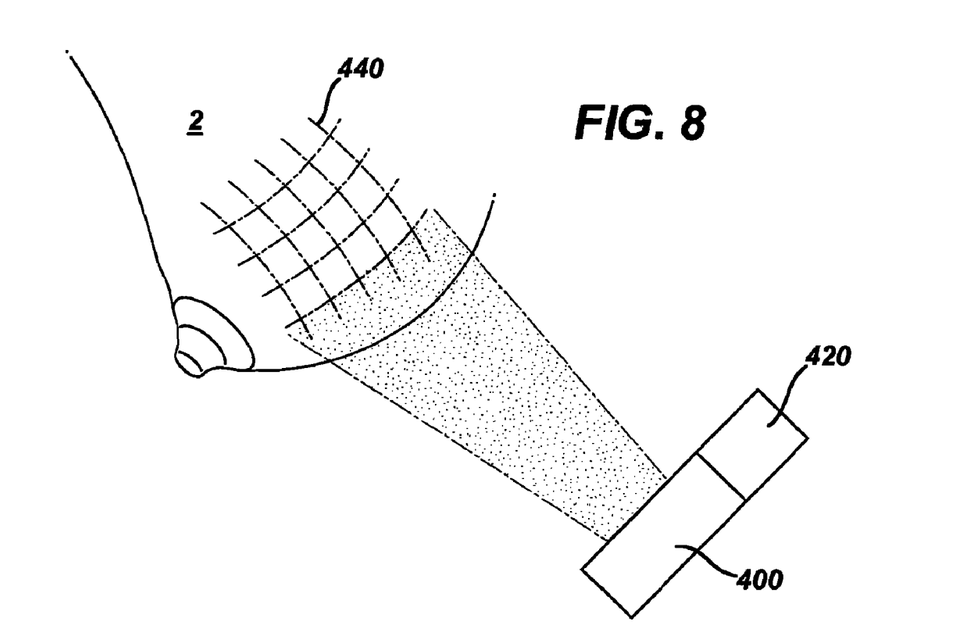
FIG. 8 is a schematic illustration of a method of forming a laser light grid pattern on patient's skin.

FIG. 8 illustrates use of one or more laser light sources to provide a grid or other pattern on the patient's skin. For instance, in MRI, PET, or BSGI procedures, it can be desirable to compress the patient's breast, such as between two surfaces, with one of the surfaces used to compress the patient's breast comprising a physical grid with regularly spaced square openings (or having other sized/shaped openings). The MRI device and associated software can be used to determine in Cartesian coordinates (e.g. X, Y) along the grid at which the biopsy needle should be inserted, as is known in the art. The biopsy needle is then inserted through openings in the grid to obtain a biopsy sample. U.S. Pat. No. 5,855,554 and U.S. Patent Publications 2008/0015429 (Tsonton et al.) and 2007/0232953 (Dietz et al) and U.S. 2007/0167736 (Dietz et al) are incorporated herein by reference in their entirety for their disclosures related to biopsy devices and accessories useful in MRI procedures.

One problem with using compression plates with ribs or slats for forming openings is that the ribs or slats may block the needle from being inserted at a point (X,Y coordinate) corresponding to a desired needle path into the breast. As illustrated in FIG. 8, a laser device 400 can be used to project a light pattern, such as a light grid 440, on the patient's breast 2. The laser device 400 can comprise one or more laser light sources for providing intersecting lines of laser light to form grid 440. An associated controller 420 can be employed to associate X and Y coordinates with the various grid lines projected on the patient, so that the light grid 440 can be used to determine the position at which the biopsy needle should be inserted. The patient's breast can be compressed, the grid 440 can be projected on the patient's skin, and the biopsy needle 30 can be inserted at the appropriate XY location using the grid 440 as a guide.

Having shown and described various embodiments of the present invention, further adaptations of the methods and systems described herein may be accomplished by appropriate modifications by one of ordinary skill in the art without departing from the scope of the present invention. Components may alternatively be described as means for providing the function performed by the component. Various modifications have been mentioned and/or will be apparent to those skilled in the art. For instance, any examples, embodiments, geometries, materials, dimensions, ratios, steps, and the like discussed above are illustrative and are not necessarily required. Accordingly, the scope of the present invention should be considered in terms of the following claims and is understood not to be limited to the details of structure and operation shown and described in the specification and drawings.

What is claimed:

1. A method of performing a medical procedure using an imaging device and a biopsy device, wherein the biopsy device includes a light source operable to directly project light distally away from the biopsy device, wherein the biopsy device comprises an elongated needle, the method comprising the steps of:
    providing a guide path on a portion of a patient, wherein the act of providing a guide path on a portion of a patient comprises directly projecting light distally from the biopsy device from the light source of the biopsy device, the projected light forming a projection extending distally along the needle, wherein the projection defines the guide path; and
    aligning the imaging device with respect to the guide path.

2. The method of claim 1, wherein the light source is positioned and configured such that the axis of the needle is aligned with the guide path and remains aligned with the guide path as the biopsy device is moved relative to the patient.

3. The method of claim 1, wherein the imaging device comprises a handheld ultrasound probe, and wherein the step of aligning comprising aligning a transducer of the ultrasound probe with the guide path.

4. The method of claim 1 wherein the step of providing a guide path comprises projecting a guide path on the patient's breast.

5. The method of claim 1 wherein the step of providing a guide path comprises projecting a light path having a maximum width of greater than 0 mm and less than 5.0 mm on the patient.

6. The method of claim 1 wherein the imaging device comprises a handheld ultrasound probe, wherein the biopsy device comprises a handheld biopsy device.

7. A method of performing a medical procedure using a biopsy device, wherein the biopsy device includes an integral light source operable to project a generally planar sheet of light distally away from the biopsy device, the method comprising the steps of:
    projecting a generally planar sheet of light from the light source of the biopsy device, wherein the generally planar sheet of light is projected distally away from the biopsy device, thereby intersecting the generally planar sheet of light with a portion of a patient's body to provide a light guide path along a portion of the patient's body; and
    aligning a portion of an imaging device with the guide path, wherein the imaging device is positioned distally in relation to the biopsy device such that the planar sheet of light is projected directly onto the aligned imaging device.

8. A method of performing ultrasound imaging of a patient's breast using an ultrasound transducer and a handheld biopsy device comprising a handpiece configured to be held and manipulated by a single hand, wherein the biopsy device further comprises a needle extending from the handpiece, and a light source operable to project a generally planar sheet of light away from the handpiece in a direction generally aligned with, or substantially parallel to, the needle, the method comprising the steps of:
    directing the light from the light source to provide a light guide path along a portion of the patient's breast, wherein the act of directing the light is performed while the handpiece is grasped in one hand by a user; and
    aligning the ultrasound transducer with respect to the light guide path, wherein the act of directing the light is performed while the ultrasound transducer is grasped in the other hand of the user.

9. The method of claim 8, wherein the light source is positioned and configured such that an axis of the needle is aligned with the light guide path and remains aligned with the light guide path as the biopsy device is moved relative to the patient.

10. The method of claim 8, wherein the step of directing the light from the light source to provide a light guide path comprises projecting a light guide path having a maximum width of greater than 0 mm and less than 5.0 mm on the patient.

* * * * *